United States Patent [19]
Choi

[11] Patent Number: 5,785,797
[45] Date of Patent: Jul. 28, 1998

[54] METHOD AND APPARATUS FOR MONITORING ETCHING BY PRODUCTS

[75] Inventor: Chang Ju Choi, Kyoungki-do, Rep. of Korea

[73] Assignee: Hyundai Electronics Industries Co., Ltd., Kyoungki-do, Rep. of Korea

[21] Appl. No.: 954,920

[22] Filed: Oct. 21, 1997

Related U.S. Application Data

[62] Division of Ser. No. 619,299, Mar. 21, 1996, Pat. No. 5,726,067.

[30] Foreign Application Priority Data

Mar. 22, 1995 [KR] Rep. of Korea .................. 95-6128

[51] Int. Cl.$^6$ ................................................ H01L 21/00
[52] U.S. Cl. ............................. 156/345; 216/60; 438/9
[58] Field of Search ............... 216/60, 85; 156/345 MT, 156/345 LT, 345 P; 438/9

[56] References Cited

U.S. PATENT DOCUMENTS

| | | | |
|---|---|---|---|
| 4,479,848 | 10/1984 | Otsubo et al. | 156/643 |
| 4,675,072 | 6/1987 | Bennett et al. | 156/643 |
| 5,002,631 | 3/1991 | Giapis et al. | 156/643 |
| 5,620,556 | 4/1997 | Henck | 438/9 X |

*Primary Examiner*—William Powell
*Attorney, Agent, or Firm*—Morgan & Finnegan L.L.P.

[57] ABSTRACT

A method of and an apparatus for monitoring etching by-products, capable of detecting and analyzing laser induced fluorescent light generated upon irradiating laser beams onto a by-product formed in the etching process. The method includes the steps of: selecting an excited electron level capable of being borne by molecules or radicals of the by-product; irradiating onto the by-product a laser beam with energy of a wavelength corresponding to the selected excited electron level; optionally exciting the molecules or radicals of the by-product by the irradiated laser beam, thereby forming a primary excited state of the by-product; detecting a laser induced fluorescent light emitted from the by-product during the transition of the by-product from the primary excited state to a secondary excited state which exhibits an energy level lower than the primary excited state; and analyzing the detected laser induced fluorescent light. The apparatus includes an etching chamber for etching a wafer therein, a laser source for irradiating a laser beam onto the wafer in the etching chamber, a plurality of reflecting mirrors for reflecting the irradiated laser beam along at least two parallel paths, and a light detector arranged outwardly of the etching chamber and adapted to detect laser induced fluorescent light generated upon irradiating the laser beam in the etching chamber.

5 Claims, 2 Drawing Sheets

5,785,797

METHOD AND APPARATUS FOR MONITORING ETCHING BY PRODUCTS

This is a divisional of co-pending application Ser. No. 08/619,299 filed Mar. 21, 1996, U.S. Pat. No. 5,726,067.

BACKGROUND OF THE INVENTION

1. Field of the Invention

The present invention relates to a method of and an apparatus for monitoring etching by-products in the fabrication of semiconductor devices, and more particularly to a method of and an apparatus for monitoring etching by-products, capable of detecting and analyzing laser induced fluorescent (LIF) light generated upon irradiating laser beams onto a by-product formed in the etching process, thereby not only achieving an accurate analysis of the etching process, but also simplifying the etching process.

2. Description of the Prior Art

In the fabrication of semiconductor devices, it is essential to analyze by-products (for example, gaseous molecules or radicals) formed in the process of etching wafers. For example, the quantitative analysis of etching by-products is an essential process required to determine an accurate etching time.

When by-products formed in the etching process are accurately analyzed, the etching process can be accurately understood. In this case, it is possible to more accurately accomplish and effectively simplify the etching process.

In most cases, however, the analysis of such etching by-products has been carried out, until lately, using an optically and naturally light-emitting method, in which the analysis is based only on the detection of radicals included in a limited amount in the etching by-products.

Furthermore, even when the analysis of the etching by-products is carried out using the optically and naturally light-emitting method, it is difficult to expect an accurate etching process unless a large amount of emitted light is generated.

Now, an example of a conventional method for monitoring etching by-products will be described in conjunction with FIG. 1.

FIG. 1 is a schematic view illustrating a conventional apparatus for monitoring etching by-products formed in an etching device.

As shown in FIG. 1, the conventional monitoring apparatus includes an etching chamber 1 in which a wafer 2 is received and etched. The monitoring apparatus also includes a monochromator 4 arranged in one side of the etching chamber 1. The monochromator 4 serves to detect light 3 naturally emitted from radicals being at an excited state upon etching the wafer 2.

In the conventional monitoring apparatus having the above-mentioned construction, the wafer 2 is etched by a reactant 5 being at an ionized state or a reactant 6 being at a molecular state. During the etching, a reaction by-product 7 is produced. The reaction by-product 7, which is radicals produced in the process of etching the water 2 and being at an excited state, emits light naturally. The naturally emitted light 13 is then detected by the monochromator 4 arranged in one side of the etching chamber 1. By this detection, the amount of radicals is measured, which is used to analyze information about the etching by-product.

However, the conventional by-product monitoring apparatus has various problems as mentioned above.

That is, it is difficult to accurately analyze the etching by-product because the analysis is based only on the detection of radicals partially included in a limited amount in the etching by-product. Furthermore, when the analysis of the etching by-product is carried out using the optically and naturally light-emitting method, it is difficult to obtain accurate information about the etching by-product unless a large amount of emitted light is generated.

SUMMARY OF THE INVENTION

Therefore, an object of the invention is to solve the above-mentioned problems involved in the prior art and to provide a method of and an apparatus for monitoring etching by-products, capable of detecting and analyzing laser induced fluorescent (LIF) light generated upon irradiating laser beams onto a by-product formed in the etching process, thereby not only achieving an accurate analysis of the etching process, but also simplifying the etching process.

In accordance with one aspect, the present invention provides a method for monitoring a by-product formed upon etching a wafer, comprising the steps of: selecting an excited electron level capable of being borne by molecules or radicals of the by-product; irradiating onto the by-product a laser beam with energy of a wavelength corresponding to the selected excited electron level; optionally exciting the molecules or radicals of the by-product by the irradiated laser beam, thereby forming a primary excited state of the by-product; detecting a laser induced fluorescent light emitted from the by-product during the transition of the by-product from the primary excited state to a secondary excited state which exhibits an energy level lower than the primary excited state; and analyzing the detected laser induced fluorescent light.

In accordance with another aspect, the present invention provides an apparatus for monitoring a by-product formed upon etching a wafer, comprising: an etching chamber for receiving a wafer therein and carrying out an etching for the wafer; a laser source for irradiating a laser beam onto an upper surface of the wafer in the etching chamber; a plurality of reflecting mirrors for reflecting the irradiated laser beam along at least two parallel paths; and a light detector arranged outwardly of the etching chamber and adapted to detect laser induced fluorescent light generated upon irradiating the laser beam in the etching chamber.

BRIEF DESCRIPTION OF THE DRAWINGS

Other objects and aspects of the invention will become apparent from the following description of embodiments with reference to the accompanying drawings in which.

DETAILED DESCRIPTION OF THE PREFERRED EMBODIMENTS

Figure 1:
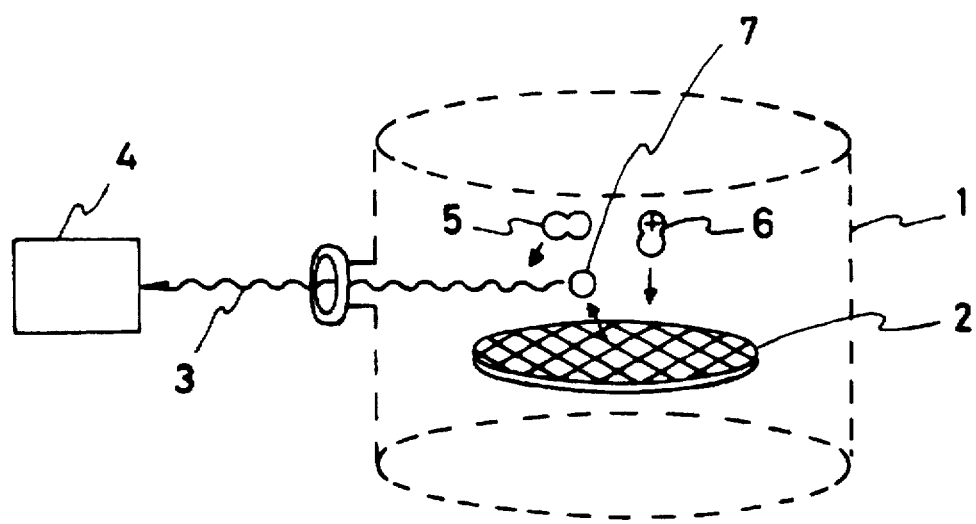
FIG. 1 is a schematic view illustrating a conventional apparatus for monitoring etching by-products formed in an etching device.
Figure 2A:
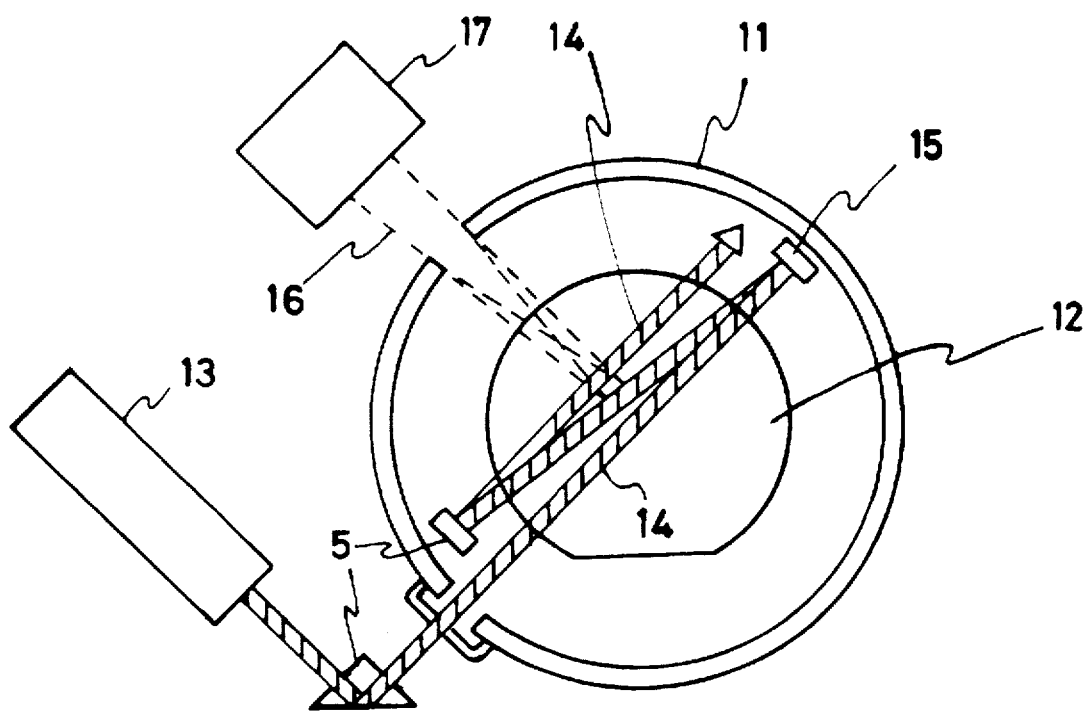
FIG. 2A is a schematic plan view illustrating an etching apparatus in which an apparatus for monitoring etching by-products in accordance with the present invention is equipped.

FIG. 2A is a schematic plan view illustrating an etching apparatus in which an apparatus for monitoring etching by-products in accordance with the present invention is equipped.

As shown in FIG. 2A, the monitoring apparatus of the present invention includes an etching chamber 11 in which a wafer 12 is received and etched. The monitoring apparatus also includes a laser source 13 for irradiating a laser beam 14 onto the upper surface of the wafer 12 in the etching chamber 11, and a plurality of reflecting mirrors 15 for reflecting the irradiated laser beam 14 along at least two parallel paths. A light detector 17 is also arranged in the outside of the etching chamber 11. The light detector 17 serves to detect LIF light 16 generated upon irradiating the laser beam 14 in the etching chamber 11.

A dye laser source is used as the laser source 13, which generates monochromatic dye laser beams. In other words, the laser source 13 preferably generates laser beams capable of tuning the wavelength of etching by-products.

The reflecting mirrors 15 are arranged inwardly and outwardly of the etching chamber 11. On the other hand, the light detector 17 is arranged outwardly of the etching chamber 11 such that it is perpendicular to the traveling direction of the laser beam 14.

A method for monitoring etching by-products formed in the etching apparatus having the above construction in accordance with the present invention will now be described in conjunction with FIGS. 2A and 2B.

Figure 2B:
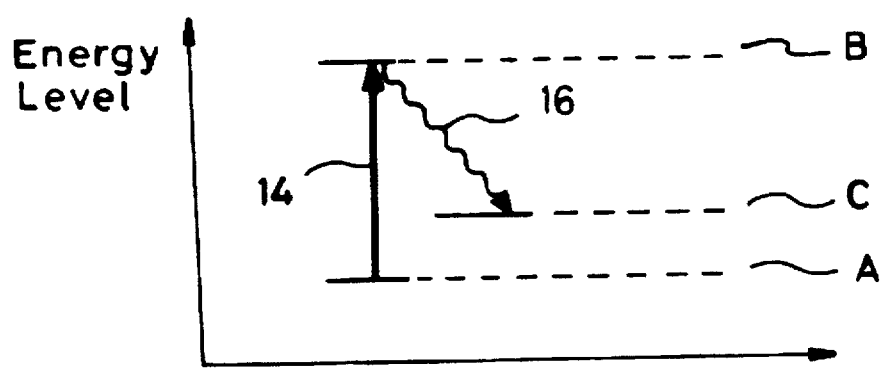
FIG. 2B is a graph illustrating the energy level of a by-product excited when it is irradiated by laser beams in the etching apparatus of FIG. 2A.

FIG. 2B is a graph illustrating the energy level of a by-product excited when it is irradiated by laser beams in the etching apparatus of FIG. 2A.

In accordance with the monitoring method of the present invention, a laser beam capable of tuning the wavelength of etching by-products, for example, a laser beam 14 from the dye laser source 13 is first irradiated onto a desired portion of the wafer 12. By the irradiation of the laser beam, a by-product formed upon etching the wafer 12 is excited. At the excited state, LIF light 16 is induced from the by-product. The LIF light 16 travels in a direction perpendicular to the traveling direction of the laser beam 14. The light detector 17 is also arranged such that it is perpendicular to the traveling direction of the laser beam 14.

In order to increase the sensitivity for the analysis of the LIF light, a plurality of reflecting mirrors 15 is arranged in the etching chamber 11 which is maintained at the vacuum state. The reflecting mirrors 15 form a plurality of paths for the laser beam 14 parallel to the wafer 12.

Thus, it is possible to amplify the strength of the LIF light 16 emitted perpendicular to the laser beam 14. For the etching by-product to be analyzed, an exciting electron level is selected, which can be borne by molecules or radicals of the etching by-product.

Using the laser source 13, energy with the wavelength corresponding to the selected excited electron level is irradiated onto the by-product, thereby optionally exciting the molecules or radicals of the by-product.

As a result, the by-product exhibits a primary excited state B, as shown in FIG. 2B. In the primary excited state B, the by-product exhibits an energy level higher than the energy level intrinsically borne therein, namely, the base state A shown in FIG. A.

The by-product then varies from the primary excited state B to a secondary excited state C within a period of about $10^{-7}$ seconds or less. At the secondary excited state C, the by-product exhibits an energy level lower than the primary excited state B and emits intrinsic light 16, namely, LIF light.

The emitted LIF light 16 is detected by the light detector 17. Based on the result of the detection, the by-product is qualitatively and quantitatively analyzed.

As apparent from the above description, the method of and apparatus for monitoring etching by-products in accordance with the present invention provide various effects.

For example, it is possible to check the figure of the actual change in material exhibited in the etching process by irradiating laser beams onto an etching by-product formed in the etching process, thereby detecting LIF light emitted from the by-product through the light detector 17. Accordingly, an accurate analysis of the etching process can be achieved by analyzing the by-product based on the result of the detection.

Since the by-product formed in the etching process can be accurately analyzed in accordance with the present invention, it is possible to rapidly carry out the preparation in advance for a new etching process. It is also possible to simplify the overall process, thereby achieving a reduction in the cost.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for monitoring a by-product formed upon etching a wafer, comprising:

an etching chamber for receiving a wafer therein and carrying out an etching for the wafer;

a laser source for irradiating a laser beam onto an upper surface of the wafer in the etching chamber;

a plurality of reflecting mirrors for reflecting the irradiated laser beam along at least two parallel paths; and a light detector arranged outwardly of the etching chamber and adapted to detect laser induced fluorescent light generated upon irradiating the laser beam in the etching chamber.

2. The apparatus in accordance with claim 1, wherein the laser beam is capable of tuning a wavelength of the etching by-product.

3. The apparatus in accordance with claim 1, wherein the laser source is a dye laser source.

4. The apparatus in accordance with claim 1 wherein the reflecting mirrors are arranged inwardly and outwardly of the etching chamber.

5. The apparatus in accordance with claim 1, wherein the light detector is arranged outwardly of the etching chamber such that it is perpendicular to the traveling direction of the laser beam.

* * * * *